United States Patent [19]

Dadoo et al.

[11] Patent Number: 5,378,334
[45] Date of Patent: Jan. 3, 1995

[54] SYSTEM FOR MEASURING AND CONTROLLING ELECTROOSMOSIS IN SEPARATION TECHNIQUES

[75] Inventors: Rajeev Dadoo, Stanford; Thomas T. Lee, Palo Alto; Richard N. Zare, Stanford, all of Calif.

[73] Assignee: The Board of Trustees of the Leland Stanford Junior University, Stanford, Calif.

[21] Appl. No.: 158,807

[22] Filed: Nov. 24, 1993

Related U.S. Application Data

[60] Continuation of Ser. No. 9,306, Jan. 22, 1993, abandoned, which is a continuation-in-part of Ser. No. 902,915, Jun. 23, 1992, abandoned, which is a division of Ser. No. 235,953, Aug. 19, 1988, abandoned, said Ser. No. 9,306, is a continuation-in-part of Ser. No. 975,850, Nov. 13, 1992, Pat. No. 5,310,463.

[51] Int. Cl.$^6$ .................... G01N 27/26; G01N 27/447
[52] U.S. Cl. .............................. 204/180.1; 204/299 R
[58] Field of Search ......................... 204/180.1, 299 R

[56] References Cited

U.S. PATENT DOCUMENTS

| | | | |
|---|---|---|---|
| 4,165,219 | 8/1979 | Huber | 23/230 R |
| 4,859,301 | 8/1989 | Brenner et al. | 204/180.1 |
| 5,069,766 | 12/1991 | Zhu et al. | 204/180.1 |
| 5,180,479 | 1/1993 | Rose, Jr. | 204/299 R |

FOREIGN PATENT DOCUMENTS 0367591  5/1990  European Pat. Off. .

OTHER PUBLICATIONS

B. J. Wanders et al "Methods for On-Line Determination and Control of Electroendosmosis in Capillary Electrochromatography and Electrophoresis" Journal of Chromatography 470 (1989) 89–93.

F. M. Everaerts et al "Feasibility of capillary zone electrophoresis with suppression of electroendosmotic flow in completely closed systems" Journal of Chromatography 503 (1990) 245–255.

Edward S. Yeung, "Self-Regulating Dynamic Control of Electroosmotic Flow in Capillary Electrophoresis" Analytical Chemistry 65 (1993) 650–652.

"On–Column Sample Concentration Using Field Amplification in CZE," by Chien et al., Analytical Chemistry, vol. 64, No. 8, pp. 489–496, Apr. 15, 1992.

"Post–Capillary Fluorescence Detection in Capillary Zone Electrophoresis Using o–phthaldialdehyde," by Rose, Jr. et al., Journal of Chromatography, vol. 447, pp. 117–131, 1988.

"Feasibility of Capillary Zone Electrophoresis with . . . ," by Verheggen et al., Journal of Chromatography, vol. 503, pp. 245–255, 1990.

"Self-Regulating Dynamic Control of Electroosmotic Flow . . . ," by Chang et al., Analytical Chemistry, vol. 65, pp. 650–652, 1993.

"Fluorescence Detection in Capillary Zone Electrophoresis . . . ," by Sweedler et al., Analytical Chemistry, vol. 63, pp. 496–502, 1991.

"Capillary Zone Electrophoretic Separation of Peptides and . . . ," by McCormick, Analytical Chemistry, vol. 60, pp. 2322–2328, 1988.

"Rapid Separation of DNA Restriction Fragments

(List continued on next page.)

*Primary Examiner*—John Niebling
*Assistant Examiner*—John S. Starsiak, Jr.
*Attorney, Agent, or Firm*—Majestic, Parsons, Siebert & Hsue

[57] ABSTRACT

An electrophoretic or chromatographic separation capillary containing a fluid or gel defines a bore therein through which a sample migrates and separates into components. The tube has a side wall defining a passage therein. A substance is introduced into the capillary through the pasage by means of gravity, pressure or electroosmosis. The substance introduced changes the electroosmotic flow rate of the fluid in the capillary tube. The electroosmotic flow rate of the fluid in the capillary tube can be monitored by introducing a compound through the passage and detecting the concentration of the compound. Information on the flow rate can be used in a feedback action to control the flow rate, such as to keep it constant.

28 Claims, 5 Drawing Sheets

OTHER PUBLICATIONS

Using . . . ," by Cohen et al., Journal of Chromatography, vol. 458, pp. 323–333, 1988.

"Influence of Borate Complexation on the Electrophoretic . . . ," by Hoffstetter-Kuhn et al., Analytical Chemistry, vol. 63, pp. 1541–1547, 1991.

"On-Column Conductivity Detector for Capillary Zone . . . ," by Huang et al., Analytical Chemistry, vol. 59, No. 23, pp. 2747–2749, 1987.

"Zone Electrophoresis in Open-Tubular Glass Capillaries," by Jorgenson et al., Analytical Chemistry, vol. 53, pp. 1298–1302, 1981.

"Capillary Zone Electrophoresis of Proteins in Un-treated . . . ," by Lauer et al., Analytical Chemistry, vol. 58, pp. 166–170, 1986.

"High Voltage Capillary Zone Electrophoresis: Operating . . . ," by Altria et al., Chromatographia, vol. 24, pp. 527–532, 1987.

"Current-Monitoring Method for Measuring the Electroosmotic Flow . . . ," by Huang et al., Analytical Chemistry, vol. 60, pp. 1 1837–1838, 1988.

"On-Line Connector for Microcolumns: Application to the On-Column . . . ," by Pentoney, Jr. et al., Analytical Chemistry, vol. 60, pp. 2625–2629, 1988.

"Factors Affecting Direct Control of Electroosmosis Using an . . . ," by Lee et al., Analytical Chemistry, vol. 63, pp. 1519–1523, 1991.

"Laser-Induced Fluorescence Detection in Capillary Zone Electrophoresis," by Nickerson et al., Chapel Hill, N.C.

SYSTEM FOR MEASURING AND CONTROLLING ELECTROOSMOSIS IN SEPARATION TECHNIQUES

CROSS-REFERENCE TO RELATED APPLICATIONS

This is a continuation of application Ser. No. 009,306 ("prior application"), filed Jan. 22, 1993 now abandoned, which is a continuation-in-part application of U.S. Ser. No. 902,915 ("First Parent Application) filed Jun. 23, 1992, now abandoned, which is a divisional application of U.S. Ser. No. 235,953, filed Aug. 24, 1988, now abandoned. U.S. Ser. No. 009,306 is also a continuation-in-part application of U.S. Ser. No. 975,850 ("Second Parent Application) filed Nov. 13, 1992 now U.S. Pat. No. 5,310,463.

BACKGROUND OF THE INVENTION

This invention relates in general to separation systems and, in particular, to a system for measuring and/or controlling electroosmosis in separation techniques.

Capillary separation techniques such as capillary zone electrophoresis (CZE) involving columns filled with liquid have become important analytical techniques for the analysis of various complex sample mixtures. When an electrolyte is introduced into a capillary column electrokinetic separation techniques, the interaction of the electrolyte with the walls of the capillary column may cause the wall to acquire a net charge. When an electrical potential is applied across the two ends of the capillary column holding the electrolyte therein, this net charge will cause the electrolyte to move under the influence of the electric field in a process known as electroosmosis. In addition, different components of the sample have different electrophoretic migration mobility under the influence of the electric field caused by the application of electrical potential across the tube. Therefore, even though the sample may include oppositely charged components migrating electrophoretically in opposite directions, if the electroosmotic flow rate is greater than the migration rate of the sample components migrating in the opposite direction to the above flow, which is usually the case, all the sample components will move in the same direction and separate into zones. Electroosmosis is employed in electrokinetic separation techniques, such as CZE and micellar electrokinetic chromatography.

The time of analysis of samples and the resolution of separation between sample components in CZE depends on the magnitude and direction of electroosmotic flow. For example, it has been shown theoretically that the best resolution between two compounds or sample components is obtained when the electroosmotic flow just counterbalances the average electrophoretic mobility of the two analytes. When this condition is met, it is possible to separate compounds with extremely small differences in mobility. Therefore, the ability to control and manipulate the electroosmotic flow may be beneficial for the separation and analysis of samples in CZE and micellar electrokinetic chromatography.

Several techniques have been developed for altering the electroosmotic flow. Such methods involve using coated or surface-modified capillaries or adding special compounds to the separation buffer. Still other methods employ coated and uncoated capillaries placed in tandem; see Nashabeh et al., *J. High Res. Chromatogr.*, Vol. 15, page 289 (1992). Yet other methods involve the application of external electric fields; see Lee et al., *Anal. Chem.*, Vol. 62, page 1550 (1990), Lee et al., *Anal. Chem.*, Vol. 63, page 1519 (1991), and Hayes et al., *Anal. Chem.*, Vol. 64, page 489A (1992).

None of the above-described methods for altering the electroosmotic flow rate is entirely satisfactory. The use of coated capillaries limits one to separation electrolytes that are compatible with the coating on the capillary surface and hence restricts the range of control of electroosmosis. For example, pH extremes cannot be employed for most coatings. Buffer additives may interact with the analytes of interest to hinder separation and to broaden peaks. This, for example, happens when tetradecyltrimethyl-ammonium bromide (TTAB) is added to negatively charged analytes. The use of multiple capillaries in tandem requires the alignment of capillary inner-channels, and also requires alterations of column lengths each time a change in the electroosmotic flow is desired. The use of external electric fields increases the complexity of instrumentation and has been shown not to work effectively under certain conditions, such as after the column has been rinsed with KOH solution. It is therefore desirable to provide an improved technique for controlling the electroosmotic flow and altering the flow rate in electrokinetic separation.

Also, when certain samples are analyzed, sample components may cause changes in the electroosmotic flow rate. For such samples, in order for the separation to be reproducible with the same results, it is important to to be able to monitor the electroosmotic flow rate in real time. It is therefore desirable to provide a design capable of monitoring the electroosmotic flow rate in real time.

SUMMARY OF THE INVENTION

The above-described difficulties are solved in the invention by employing a separation capillary tube with a passage in its side wall, and by introducing a substance into the separation capillary through the passage. The substance is one that would alter the electroosmotic flow of the electrolyte in the capillary.

One aspect of the invention is directed towards an apparatus for separating a sample into its components. The apparatus comprises a capillary tube defining a separation channel therein for holding an electrolyte and the sample, and a device for applying electrical potential across a section of the channel causing the sample to migrate and separate into its components, and a substance that alters the electroosmotic flow rate of the electrolyte and the sample in the section when present in the channel. The tube has a sidewall defining at least one passage therein that permits the substance to pass from outside the tube to the channel. The apparatus further comprises means for introducing the substance into the channel through the passage.

Another aspect of the invention is directed towards a method for electrokinetic separation of a sample in a separation column containing the sample and an electrolyte. The column has an inlet and an outlet and a passage between the inlet and the outlet. The method comprises applying an electric field in the column to cause electroosmotic flow of the electrolyte and the sample to migrate and separate in a section of the column into its components, and introducing a substance into the column through the passage to alter the electroosmotic flow rate in the column.

Another aspect of the invention is directed towards an apparatus for monitoring and/or controlling the electroosmotic flow rate of an electrolyte and sample during an electrokinetic separation. This apparatus comprises a capillary tube defining a separation channel therein for holding an electrolyte and a sample, a device for applying electrical potential across a section of the channel causing the sample to migrate and separate into its components and a substance that is diluted by the electrolyte when introduced through a passage in the tube so that concentration of the substance in the electrolyte varies with the electroosmotic flow rate of the electrolyte and the sample in the section. The tube has a sidewall defining at least one passage therein that permits the substance to pass from outside the tube to the channel. The appartus further comprises means for introducing a substance into the channel through the passage and a first detector for detecting the concentration of the substance to determine the electroosmotic flow rate of the electrolyte and the sample in the section.

Another aspect of the invention is directed towards a method for monitoring and/or controlling electroosmotic flow rate of a sample during electrokinetic separation of the sample in a separation column containing the sample and an electrolyte, said column having an inlet and an outlet and a passage between the inlet and the outlet. The method comprises applying an electric field in the column to cause electroosmotic flow of the electrolyte and the sample, and to cause the sample to migrate and separate in the section of the column into its components, introducing a substance into the column through the passage so that the substance is diluted by the electrolyte and so that concentration of the substance is a function of the electroosmotic flow rate of the sample in the column. The method further comprises detecting a parameter indicating the concentration of the substance to detect the electroosmotic flow rate of the sample in the column.

DETAILED DESCRIPTION OF THE PREFERRED EMBODIMENTS

Figure 1:
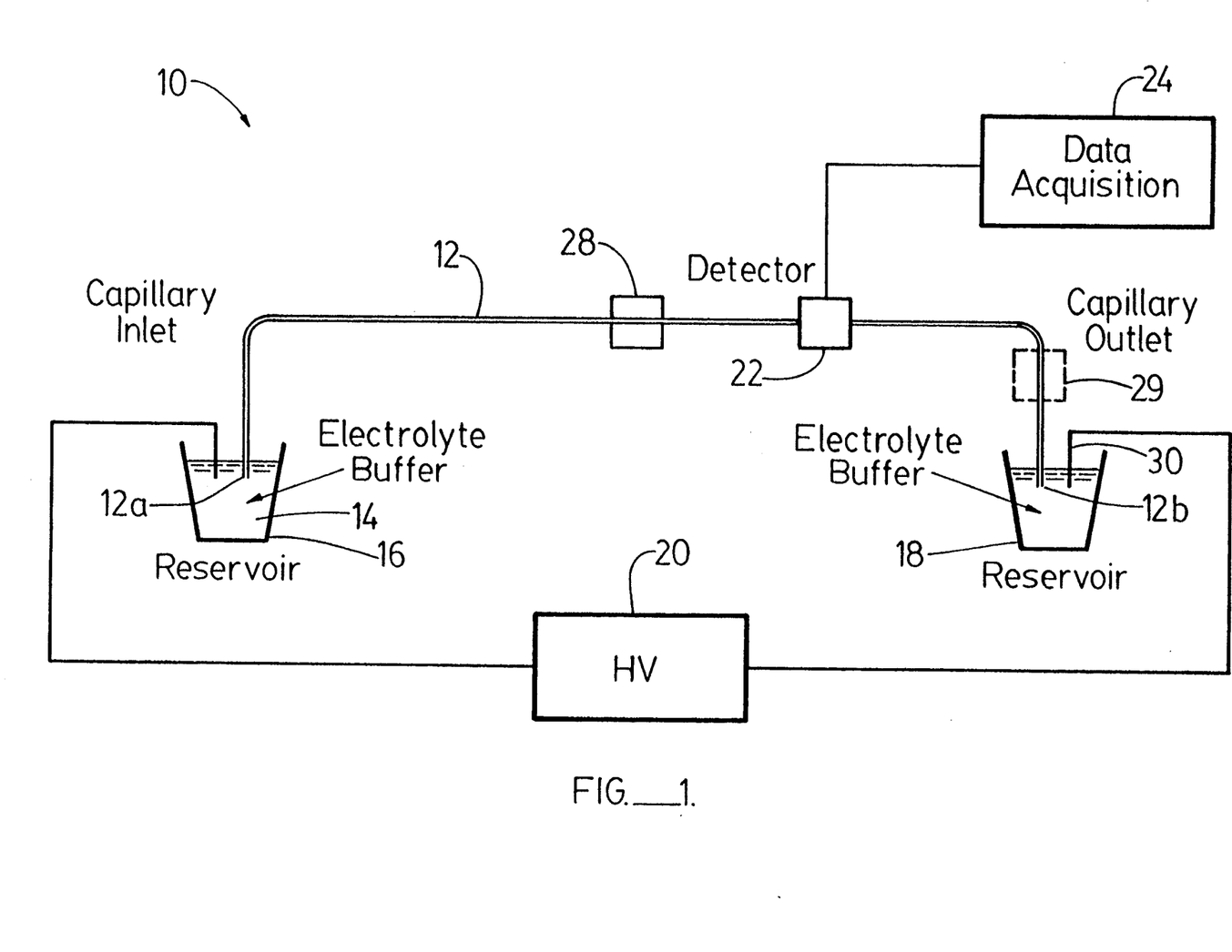
FIG. 1 is a schematic view of a capillary electrophoretic system useful for illustrating the invention.

FIG. 1 is a schematic view of a capillary electrophoretic system useful for illustrating the invention. As shown in FIG. 1, apparatus 10 includes a capillary tube 12 with an inlet end 12a and an outlet end 12b. An electrolyte buffer 14 is supplied to the tube to end 12a from a reservoir 16. The electrolyte buffer which exits from outlet end 12b is collected in reservoir 18. A high voltage is applied between the two reservoirs, causing the electrolyte to move from reservoir 16 through inlet end 12a, capillary tube 12, and end 12b to exit in the reservoir 18. The high voltage is applied by a voltage supply 20. As is known in conventional capillary electrophoresis, a sample is introduced into the inlet end 12a, such as by dipping end 12a for a short time into a sample and applying a voltage across the tube to move a small portion of the sample into the tube. The end 12a is then dipped in the reservoir 16, where the portion of the sample is then carried under the influence of the electric field through tube 12 towards end 12b. As is also known in the electrophoretic art, different components of the sample may move with different speeds in tube 12, causing the components to separate along the length of the tube. These components are detected by detector 22 when the components pass the detector. Signals from detector 22 are sent to a data acquisition system 24 for analysis and recording.

Figure 2:
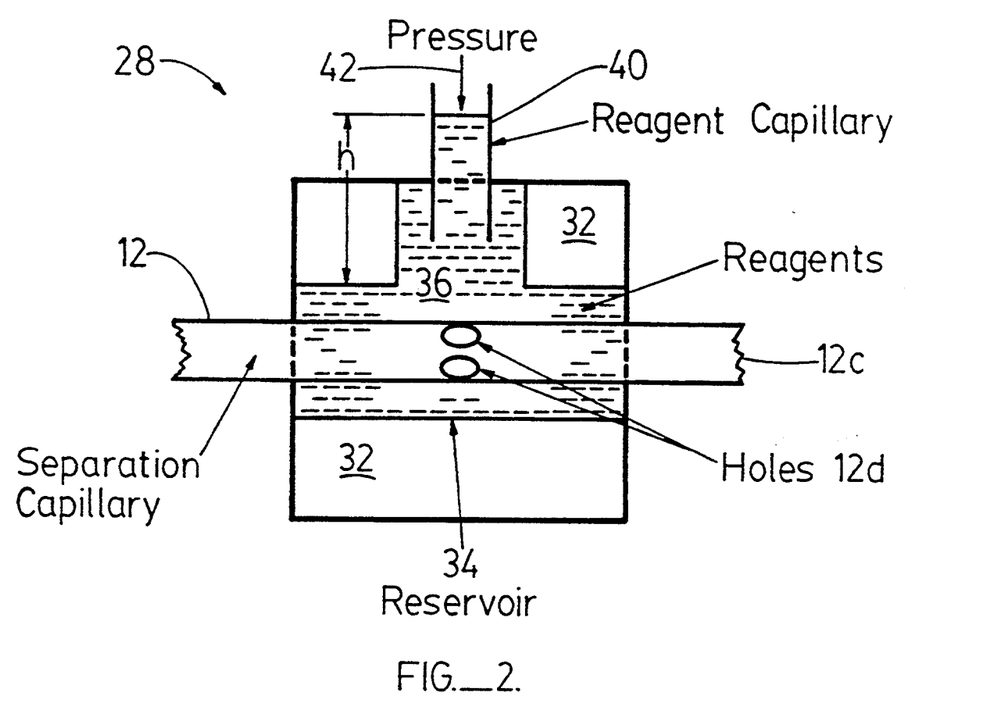
FIG. 2 schematic view of a section of the separation capillary and a system for introducing a substance into the separation capillary of FIG. 1 to illustrate a first embodiment of the invention.

In order to affect the sample analysis and migration such as by altering the electroosmotic flow rate, the scheme for introducing substances of the Second Parent Application is employed as described below in reference to FIGS. 1, 2 and 3. The description below is taken from the Second Parent Application. In such scheme, one or more holes (not shown in FIG. 1) are provided in capillary tube 12 as well as a system 28 (shown also in dotted line position 29 in FIG. 1 for reasons explained below) illustrated in more detail in FIG. 2 in the first embodiment. As shown in FIG. 2, the separation capillary 12 has a side wall 12c defining two through holes 12d therein. A section of the separation capillary 12 is enclosed by a housing 32 defining a reservoir 34 therein for holding a fluid 36 which surrounds the holes 12d. The fluid 36 contains a substance or reagent which is to be introduced into the capillary 12. For convenience in description, identical components in this application in the different figures are labeled by the same numerals.

The substance or reagent which is to be introduced into the capillary 12 may be introduced by a number of mechanisms, including gravity, pressure or electroosmosis. This is illustrated in FIG. 2, where the level of the reagent in a reagent capillary 40 is raised to height h above the level of capillary 12, so that the hydrostatic pressure would cause the reagents in reservoir 34 to enter capillary 12 through holes 12d.

As shown in FIG. 2, between housing 32 and capillary 12 at the two ends of the housing are two annular spaces therebetween. These spaces may be sealed by means of epoxy or other sealants or, alternatively, they may be sealed using a screw plug type mechanism known to those skilled in the art. The annular space between housing 32 and capillary 40 may be sealed in a similar manner. The reagent in the reservoir 34 may then be replenished through capillary 40. Alternatively, if the level of the reagent in reservoir 34 is at a sufficient height above the holes 12d, capillary 40 may be omitted and replaced by a channel (not shown) for replenishing the reagent. Instead of using gravity injection as explined above in reference to FIG. 2, the reagents may also be introduced into the capillary 12 by pressure, such as by applying pressure through capillary 40 so that the pressure in capillary 40 and reservoir 34 is at a higher pressure than that within capillary 12. This is illustrated symbolically by the arrow 42 in FIG. 2. Alternatively, pressure may be applied directly to the reagent in reservoir 34 without capillary 40.

Figure 3:
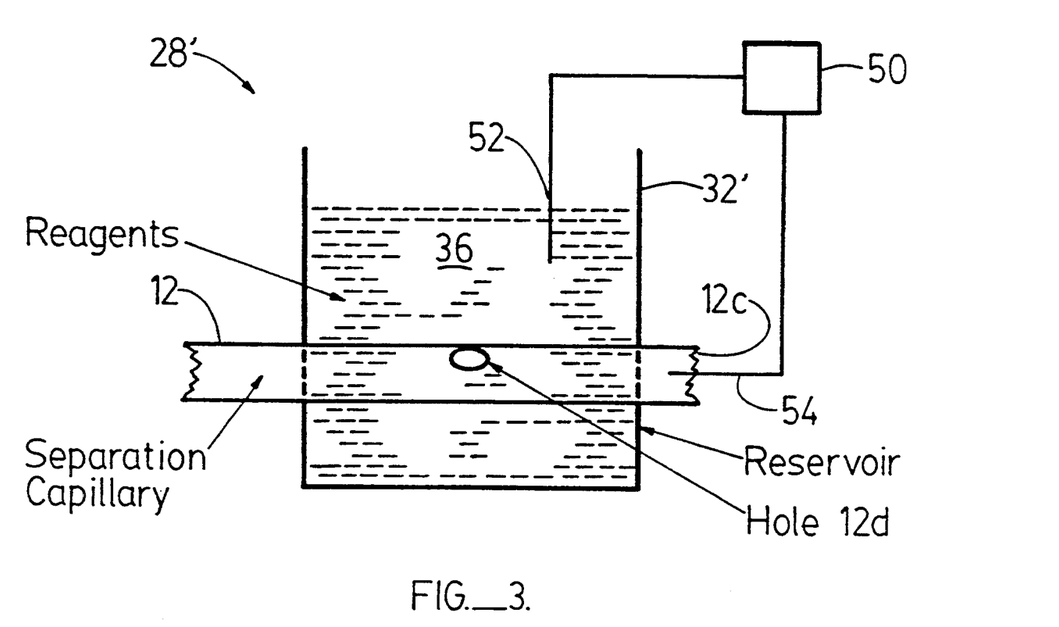
FIG. 3 is a schematic view of a section of the separation capillary and a system for introducing a substance into the separation capillary to illustrate a second embodiment of the invention.

FIG. 3 is a schematic view of a system for introducing a substance into a separation capillary to illustrate a slightly altered scheme compared to that of FIG. 2. The side wall 12c of capillary 12 has only one hole 12d instead of two as in FIG. 2. It will be understood, however, that side wall 12c may define therein more than one or two holes for introduction of the reagent. Housing 32' encloses a reservoir for holding a reagent 36. In addition to gravity and pressure, the reagent may be introduced into the capillary 12 by means of electroosmosis, such as by applying a voltage between the reagent in the reservoir and one end of the capillary 12, such as by using voltage supply 50 through an electrode 52 dipped in reagents 36 in the reservoir and another electrode 54 electrically connected to the contents in tube 12, such as by being connected to electrode 30 of FIG. 1 for convenience. In the preferred implementation, the high voltage supply 20 between the inlet and outlet reservoirs 16, 18 is turned off when voltage supply 50 is turned on to supply a potential difference between electrodes 52, 54. In such event, the section of the tube 12 between hole 12d and the outlet end 12b may be treated as a capillary separate from the section upstream from hole 12d, and the potential difference between electrodes 52, 54 will cause an electroosmotic flow from hole 12d towards end 12b. Preferably, voltage supplies 20, 50 are turned on alternately so that only one is on at any one time. When supply 20 is on, the potential applied will cause migration and separation of the sample. When supply 50 is on, a reagent is introduced into hole 12d to affect the electroosmotic flow rate.

As illustrated in FIG. 1, holes 12d and the system for introducing a substance into the capillary may be located upstream from detector 22 at solid line position 28. After setting forth above the scheme for introducing substances described in the Second Parent Application, we now return to the invention for altering the electroosmotic flow in CZE and micellar electrokinetic chromatography.

Where the substance introduced would adversely affect the separation, analysis or detection of the sample, it may be desirable to introduce the substance after such separation, analysis or detection has been completed. As shown in FIG. 1, the separation, analysis and detection are completed when the sample components migrate past detector 22. The section of the capillary from end 12a up to the portion adjacent to detector 22 is hence the section where separation, analysis and detection take place. Thus, instead of being at location 28 as shown in solid line in FIG. 1, the systems for introducing the substance such as that shown in FIGS. 2 and 3 and described above may instead be employed at dotted position 29 shown in dotted lines in FIG. 1. When it is introduced at such location, the substance introduced would merely flow or migrate through the section of the capillary tube 12 between location 29 and end 12b, thereby not directly interacting with the electrolyte or sample components prior to the detection of the components possible. It is possible to affect the electroosmotic flow rate in capillary 12 upstream from location 29, since the net electroosmotic flow in the entire column in capillary 12 is a weighted average of the electroosmotic flow rate in different parts of the column. See Chien et al., Anal. Chem., Vol. 64, page 489A (1992). To alter the electroosmotic flow rate, this may be accomplished by a change in ion concentration, a change in pH, or the addition of compounds that affect electroosmotic flow (e.g., TTAB, divalent metal ions). While for many purposes it is most useful to have the detector located upstream from the system at location 29, where the substance introduced does not interfere with the separation, analysis or detection, the substance may be introduced upstream from the detector such as at solid line location 28 in FIG. 1. This method offers users the ability to independently control electroosmosis while being able to choose the best possible electrolyte for the separation. It also avoids unwanted interactions between the sample analytes and the additive used to control the electroosmotic flow, where separation and detection are completed before the additive is introduced into the column. No significant change in instrument complexity is required to employ this method.

Figure 4:
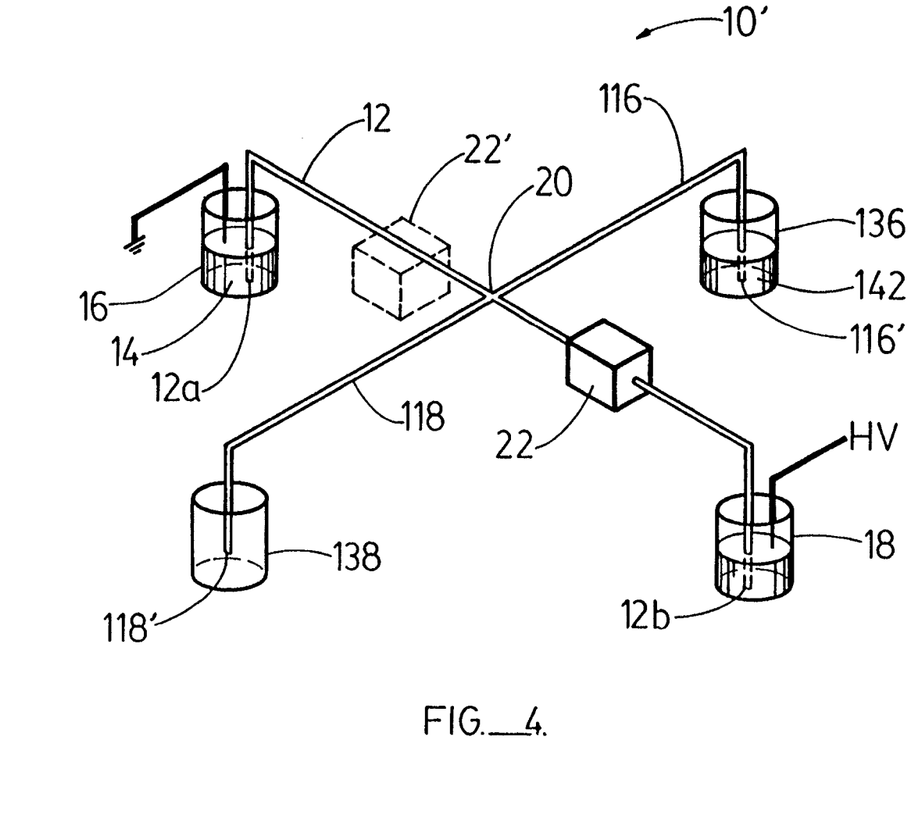
FIG. 4 is a schematic view of a capillary electrophoretic system useful for illustrating a third embodiment of the invention.

Embodiments other than those of FIGS. 2 and 3 are also possible. One such embodiment is illustrated in the T- or cross connector of the First Parent Application. FIG. 4 is a schematic view of the capillary electrophoretic system useful for illustrating the invention using the T- or cross connector of the First Parent Application. Different from the embodiments of FIGS. 1-3, the T- or cross connector of FIG. 4 enables a substance to be introduced into the main separation capillary by actually employing a structure with a main capillary tube equipped with one or two side branch tubes. In FIG. 4, two branch tubes 116 and 118 are used. In the same manner as that described in reference to FIG. 1, electrical potential applied between the two electrolyte buffers in reservoirs 16 and 18 cause the electrolyte and sample to migrate through capillary 12 from reservoir 16 towards reservoir 18. During the migration, the sample separates into its components which are then detected by detector 22. In order to introduce a substance into the main separation capillary 12, a liquid 142 containing a substance is placed in container 136 and container 136 is placed at a higher elevation than container 138. After liquid 142 is introduced inside tube 116, it will flow towards connection 20 to side tube 118 and is subsequently discharged into container 138. Since the space enclosed by the two side tubes 116, 118 is connected to the space enclosed by the main capillary 12 at connection 20, a small portion of the liquid 142 will become mixed with the portion of the electrolyte and sample in the main capillary and the mixture will flow through capillary 12 towards reservoir 18. The substance introduced alters the electroosmotic flow rate and therefore aids the separation and analysis of the sample.

In FIG. 4, connection 20 is upstream from the detector 22 shown in solid lines. For reasons explained above, it may be desirable to introduce the substance downstream from the detector, after detection of the separated sample components is performed. For this purpose, the detector may be placed at dotted line position 22' instead in FIG. 4.

Figure 5A:
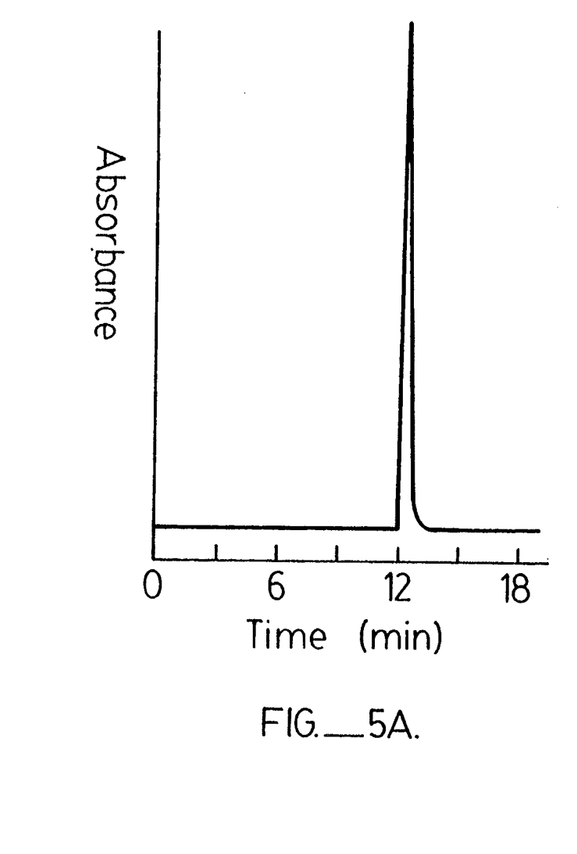
FIG. 5A shows an electropherogram of a neutral marker (mesityl oxide) when a 20 mM borate buffer is used as the separation electrolyte.
Figure 5B:
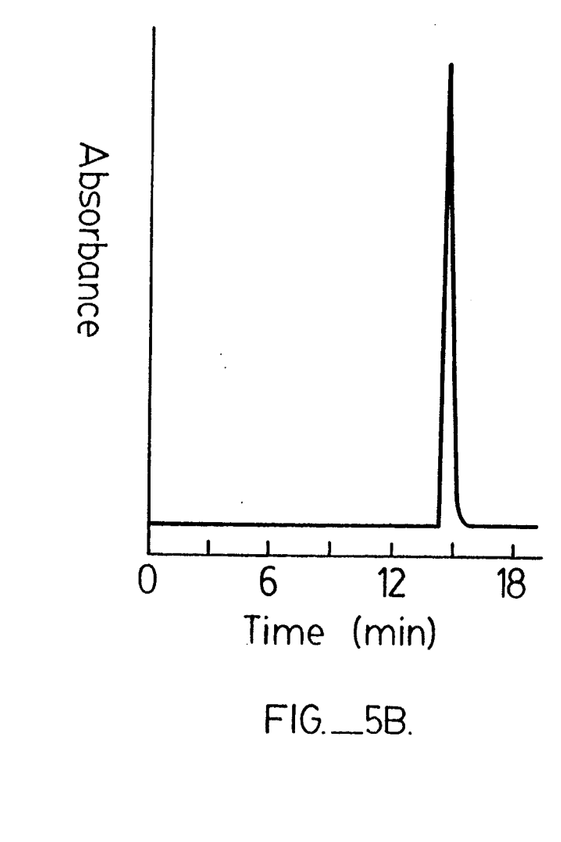
FIG. 5B shows an electropherogram of the same compound (i.e., mesityl oxide) when a 10 mM TTAB solution is delivered to the separation capillary using the system of this invention.

The alteration of the electroosmotic flow using the system of this invention is illustrated in FIGS. 5A, 5B.

FIG. 5A shows an electropherogram of a neutral marker (mesityl oxide) when a 20 mM borate buffer was used as the separation electrolyte. FIG. 5B shows an electropherogram of the same compound when a 10 mM TTAB solution (in the borate buffer) was delivered to the junction (and hence, the separation capillary) by the reagent capillary. Thus, the addition of TTAB to the latter part of the separation capillary slowed down electroosmosis in the entire capillary including the part upstream from the substance introduction system at location 29, not just the part of the capillary downstream from such system.

Further details in the experiment illustrated in FIGS. 5A, 5B are as follows. An ISCO (CV[4]) absorbance detector was used for the experiments. A T-junction was made using a 100 μm i.d. separation capillary with two holes drilled using a $CO_2$ laser (as described in Pentoney et al., Anal. Chem., Vol. 60, page 2625 (1988). The length of the separation capillary was 75 cm (40 cm from inlet to detector and a further 10 cm from detector to the T-junction). The reagent capillary was 70 cm in length (200 μm i.d.). The T was manufactured as shown in FIG. 1 with the reagent capillary not directly attached to the separation capillary. For the electropherogram shown in FIG. 5A, a 20 mM sodium borate (pH 9.2) buffer was used for the run. The reagent reservoir (containing the borate buffer also) was placed 6 cm above the electrophoresis reservoirs. For FIG. 5B, the only change was that of changing the solution in the reagent reservoir to that containing 10 mM TTAB. The applied voltage was 12 kV with the detect ion performed at 254 nm for both runs. The sample (0.5% mesityl oxide in buffer) was injected by gravity for 5s with the sample vial held 10 cm above the buffer reservoirs.

Figure 6:
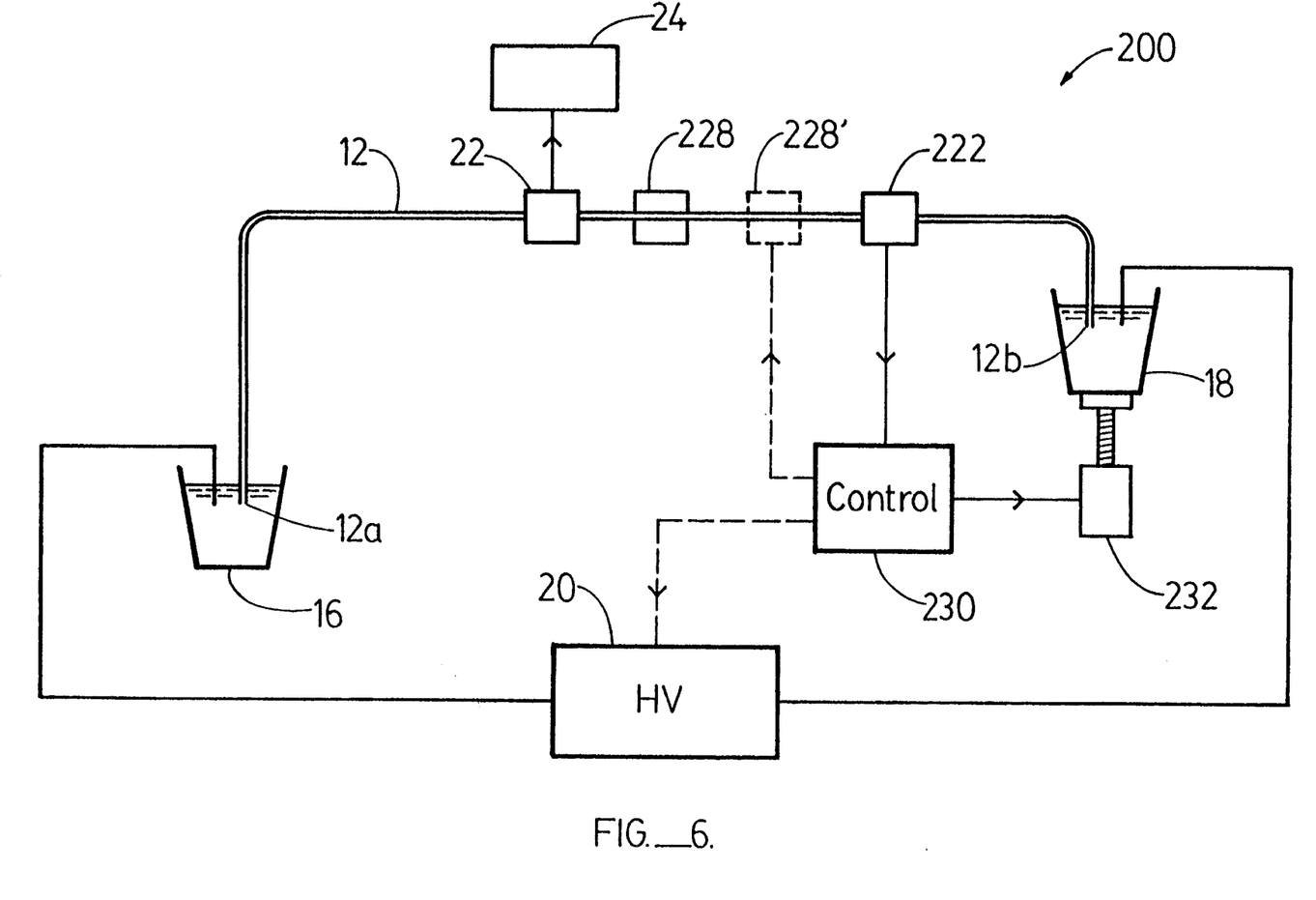
FIG. 6 is a schematic view of a capillary electrophoretic system for monitoring the electroosmotic flow rate of an electrolyte and a sample during separation and for controlling the flow rate to illustrate a fourth embodiment of the invention.

When certain samples are analyzed, sample components may cause changes in the electroosmotic flow rate. In such event, in order for the separation to be reproducible with the same results, it is important to be able to monitor the electroosmotic flow rate in real time, so that, if desired, the flow rate can be maintained at the same rate during different runs. FIG. 6 is a schematic view of an electrophoretic system illustrating how the electroosmotic flow rate may be monitored in real time. As shown in FIG. 6, an electric field is applied across ends 12a, 12b of capillary tube 12 by means of buffers in reservoirs 16, 18 and high voltage supply 20. The separated components are detected by detector 22 and recorded in data acquisition unit 24 in the same manner as described above in reference to FIG. 1. Capillary tube 12 defines at least one passage therein that permits injection of a substance by means of a structure 228, where structure 228 is one of the type shown in FIGS. 2-4 used to inject a substance or compound in a solution form through the passage into the channel inside tube 12. The solution is introduced by structure 228 at a substantially constant rate. When the solution enters the channel tube 12, it is diluted by the electrolyte in the channel, and the resulting concentration of the solution introduced by structure 228 downstream from the structure depends on the electroosmotic flow rate of the electrolyte in the channel. Hence, by measuring the concentration of the compound that has been introduced through the passage by structure 228 continuously during a run, one obtains in real time the bulk flow rate in the separation part of the column (between inlet 12a and detector 22) continuously during the run also.

Passage or junction (at structure 228, but passage or junction not shown in FIG. 6) in tube 12 is placed after the separation and detection of the sample analytes by detector 22 in order to avoid any interferences that the compound or substance introduced by structure 228 might create otherwise. Also, in the case where the sample analytes influence the electroosmotic flow in the part of the column after the junction (e.g., by adsorbing to the walls, etc.), the column may be grounded (not shown in FIG. 6) right before the junction or passage to avoid these effects on the measurement. This may be accomplished through a structure that permits electrical contact such as described in U.S. Pat. No. 4,908,116 or "Capillary Zone Electrophoresis with Electrochemical Detection," Anal. Chem., 1987, 59, 1762-1766 and "Amperometric Detection of Catechols in Capillary Zone Electrophoresis with Normal and Micellar Solutions," Anal. Chem., 1988, 60, 258-263, Wallingford et al.

The above-described method offers one the ability to dynamically monitor the electroosmotic flow continuously during separations and also allows the possibility of using a feedback mechanism to control the electroosmotic flow. This is illustrated in FIG. 6 as described below.

The concentration of the substance or compound introduced by structure 228 is detected by a second detector 222. Detector 222 generates an output signal which indicates the concentration of the substance or compound detected and sends such signal to control unit 230. Thus if the substance changes the light absorbence or fluorescence characteristic of the electrolyte, such changes may be detected by an absorbence or fluorescence detector; such changes indicate changes in concentration of the substance in the electrolyte in the tube. Detector 222 then generates an output signal indicating such changes in light absorbence or fluorescence which in turn indicates changes in concentration of the substance. To obtain the correlation between changes in light absorbence or fluorescence on one hand and concentration of the substance on the other, the system is first calibrated by passing in separate runs electrolytes with different known concentrations of the substance through the capillary and detecting the resluting light absorbence or fluorescence.

In response to an output signal from detector 222, control unit 230 then generates a control signal (such as by amplifying the output signal) and applies it to a screw 232 for raising or lowering reservoir 18, thereby changing the hydrostatic pressure in capillary 12 in order to alter the bulk flow rate of the electrolyte between inlet end 12a and detector 22. Alternatively, the electroosmotic flow rate may be altered by introducing a substance in a manner described above in reference to FIGS. 1-4, 5a, 5b by using a second structure 228', where structure 228' may be one similar to those in FIGS. 2-4. If structure 228' is similar to that shown in FIG. 3, then the control signal for control unit 230 may be applied to a voltage supply unit similar to voltage supply 50 of FIG. 3, for altering the electrical potential applied across a portion of tube 12 (e.g. between hole 12d and end 12b of tube 12), thereby altering the rate the substance for altering the electroosmotic flow rate is introduced into the capillary channel. If structure 228' is similar in structure to that in either FIGS. 2 or 4, a screw mechanism such as one similar to 232 may be employed. Yet another alternative is to cause control unit 230 to apply a control signal to high voltage supply 20 in order to alter the electrical potential applied across ends 12a, 12b of the capillary tube in order to alter the electroosmotic flow rate. Where a constant target bulk flow rate is desired, the control unit compares the output signal of detector 222 to a preset value corresponding to the desired bulk flow rate and derives an error signal that is used to control screw 232, a similar screw for controlling structure 228' or voltage supply 20, in order to zero out the error signal.

While the invention has been described above by reference to various embodiments, it will be understood that various modifications and changes may be made without departing from the scope of the invention which is to be limited only by the appended claims. For example, instead of employing structures such as those shown in FIGS. 2–4 for introducing substances, other structures are possible such as that described in the article by Rose, Jr., D. J.: Jorgenson, J. W., *J. Chromatog.*, 1988, 447, 117.

What is claimed is:

1. An apparatus for separating a sample into its components, comprising:
    a capillary tube defining a separation channel therein for holding an electrolyte and the sample;
    device for applying electrical potential across a section of the channel causing the sample to migrate and separate into its components;
    a substance that alters the electroosmotic flow rate of the electrolyte and the sample in the section when present in the channel, said tube having a side wall defining at least one passage therein that permits said substance to pass from outside the tube to said channel; and
    means for introducing said substance into the channel through the passage.

2. The apparatus of claim 1, further comprising a detector adjacent to the separation channel for detecting the separated sample components, said detector located upstream or downstream from the passage.

3. The apparatus of claim 2, said detector located upstream from the passage, so that the section is a portion of the channel upstream from the detector, and so that the substance does not interact directly with the sample components in the section or their detection.

4. The apparatus of claim 1, said introducing means including means for applying a pressure differential or electrical potential across a portion of the tube.

5. A method for electrokinetic separation of a sample in a separation column containing the sample and an electrolyte, said column having an inlet and an outlet and a passage between the inlet and the outlet, said method comprising:
    applying an electric field in the column to cause electroosmotic flow of the electrolyte and the sample to migrate and separate in a section of the column into its components; and
    introducing a substance into the column through said passage to alter the electroosmotic flow rate of the sample in the column.

6. The method of claim 5, further comprising detecting the separated sample components at a location adjacent to the separation channel.

7. The method of claim 6, wherein said passage is downstream from said location, so that the substance is introduced by the introducing step downstream from the location so that the substance does not interact directly with the sample components in the section or their detection.

8. The method of claim 5, wherein said passage is downstream from said location, so that said introducing step introduces the substance into the column downstream from the section, and so that the substance introduced does not interact directly with the sample in the section.

9. The method of claim 5, said column being a capillary tube defining a separation channel therein containing a sample and an electrolyte, said tube having a side wall defining at least one passage therein that permits the passage of the substance, wherein said introducing step introduces said substance through said passage into the channel to alter the electroosmotic flow rate of the sample in the channel.

10. The method of claim 9, wherein said introducing step includes the step of applying pressure, gravity or electrical potential across a portion of the column.

11. An apparatus for monitoring and/or controlling electroosmotic flow rate of an electrolyte and a sample during separation of the sample into its components in an electrokinetic separation process, comprising:
    a capillary tube defining a separation channel therein for holding an electrolyte and the sample;
    device for applying electrical potential across a section of the channel causing the sample to migrate and separate into its components;
    a substance that is diluted by the electrolyte when introduced through a passage in the tube so that the concentration of the substance in the electrolyte in the tube varies with the electroosmotic flow rate of the electrolyte and the sample in the section when present in the channel, said tube having a side wall defining at least one passage therein that permits said substance to pass from outside the tube to said channel;
    means for introducing said substance into the channel through the passage; and
    a first detector for detecting a parameter indicating the concentration of said substance to determine the electroosmotic flow rate of the electrolyte and the sample in the section.

12. The apparatus of claim 11, further comprising a second detector adjacent to the separation channel for detecting the separated sample components, said second detector located upstream or downstream from the passage.

13. The apparatus of claim 12, said second detector located upstream from the passage, so that the section is a portion of the channel upstream from the detector, and so that the substance does not interact directly with the sample components in the section or their detection.

14. The apparatus of claim 11, said introducing means including means for applying a pressure differential or electrical potential across a portion of the tube.

15. The apparatus of claim 1, further comprising feedback means responsive to the parameter indicating the concentration of the substance detected by the first detector for altering the bulk flow rate of the electrolyte and the sample in the section.

16. The apparatus of claim 15, said feedback means causing the electrical potential applied by the device to change so as to maintain a target bulk flow rate of the electrolyte and the sample in the section.

17. The apparatus of claim 15, further comprising means for altering the electroosmotic flow rate of the electrolyte and the sample in the section.

18. The apparatus of claim 17, wherein said altering means includes a second substance that changes the electroosmotic flow rate of the electrolyte when present in the tube.

19. The apparatus of claim 18, the side wall of said tube defining a second passage therein that permits the passing of the second substance from outside the tube to the channel through the second passage.

20. The apparatus of claim 17, wherein said altering means includes means for applying a pressure differential across the tube.

21. The apparatus of claim 17, wherein said first detector generates an output signal, said feedback means applying the first detector output signal to the altering means so as to control the electroosmotic flow rate of the electrolyte and the sample in the tube.

22. A method for monitoring and/or controlling electroosmotic flow rate of a sample during electrokinetic separation of the sample in a separation column containing the sample and an electrolyte, said column having an inlet and an outlet and a passage between the inlet and the outlet, said method comprising:

applying an electric field in the column to cause electroosmotic flow of the electrolyte and the sample, and cause the sample to migrate and separate in a section of the column into its components;

introducing a substance into the column through said passage, so that said substance is diluted by the electrolyte and so that concentration of the substance is a function of the electroosmotic flow rate of the sample in the column;

detecting a parameter indicating the concentration of the substance to detect the electroosmotic flow rate of the sample in the column.

23. The method of claim 22, wherein the separated components are detected at a location along the tube, and wherein the introducing step introduces the substance downstream from the location and so that the substance does not interact directly with the sample components prior to their detection.

24. The method of claim 22, said introducing step including applying a pressure differential or electrical potential across a portion of the column.

25. The method of claim 22, further comprising altering the electroosmotic flow rate of the electrolyte and the sample in response to the parameter indicating the concentration of the substance detected in a feedback action to control the bulk flow rate of the electrolyte and the sample.

26. The method of claim 25, said altering step causes the electrical potential applied in the applying step to change so as to maintain a target electroosmotic flow rate of the electrolyte and the sample.

27. The method of claim 25, wherein said altering step includes introducing a second substance that changes the electroosmotic flow rate of the electrolyte and the sample in the tube, the side wall of said tube defining a second passage therein that permits the passing of the second substance from outside the tube to the channel through the second passage.

28. The method of claim 27, wherein said altering step includes applying a pressure differential across the tube.

* * * * *